(12) United States Patent

Crabtree et al.

(10) Patent No.: US 9,168,156 B2
(45) Date of Patent: Oct. 27, 2015

(54) TRIAL COUPLER SYSTEMS AND METHODS

(75) Inventors: Paul Charles Crabtree, Nesbit, MS (US); Roger Ryan Dees, Senatobia, MS (US); Mark Ellsworth Nadzadi, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1501 days.

(21) Appl. No.: 12/159,858

(22) PCT Filed: Oct. 31, 2006

(86) PCT No.: PCT/US2006/042706
§ 371 (c)(1),
(2), (4) Date: Jan. 14, 2009

(87) PCT Pub. No.: WO2007/114841
PCT Pub. Date: Oct. 11, 2007

(65) Prior Publication Data
US 2009/0306787 A1   Dec. 10, 2009

Related U.S. Application Data

(60) Provisional application No. 60/789,177, filed on Apr. 4, 2006.

(51) Int. Cl.
    *A61F 2/38*    (2006.01)
    *A61F 2/46*    (2006.01)
    *A61F 2/30*    (2006.01)

(52) U.S. Cl.
    CPC ............. *A61F 2/4684* (2013.01); *A61F 2/4637* (2013.01); *A61F 2/30721* (2013.01);
    (Continued)

(58) Field of Classification Search
    CPC ......... A61F 2/3859; A61F 2/389; A61F 2/38; A61F 2/30721; A61F 2/4637; A61F 2/4684; A61F 2002/4642
    USPC ................. 606/300, 325, 328, 86 R, 90, 102; 623/20.14, 20.15, 20.21, 20.32–20.36; 403/292, 293, 296, 299, 300, 301, 305, 403/306
    See application file for complete search history.

(56) References Cited

U.S. PATENT DOCUMENTS 621,456 A * 3/1899 Jamieson ...................... 411/314
2,290,056 A * 7/1942 Koubek ........................ 411/313

(Continued)

FOREIGN PATENT DOCUMENTS

EP  0 714 645 A1  6/1996
EP  0 853 930 A2  7/1998
EP  0 993 813 A2  4/2000

OTHER PUBLICATIONS

International Search Report dated Feb. 28, 2007 in related Application No. PCT/US2006/042706.

(Continued)

*Primary Examiner* — Michael T Schaper
(74) *Attorney, Agent, or Firm* — Fish & Richardson P.C.

(57) ABSTRACT

Embodiments of the present invention provide a trial coupler system for use in preparing a patient for an implant. Certain embodiments provide a system including a coupling device (20) and a trial component interface (40) that allows a trial stem (100) to be offset in relation to the respective trial components at an orientation that matches the geometry of the patient. Once the precise positioning is obtained, the trial coupler device (10) can be locked while on the patient's bone so the assembly can be removed without disturbing the desired orientation.

39 Claims, 4 Drawing Sheets

(52) U.S. Cl.
CPC .............. *A61F 2/389* (2013.01); *A61F 2/3859* (2013.01); *A61F 2002/30354* (2013.01); *A61F 2002/30507* (2013.01); *A61F 2002/30604* (2013.01); *A61F 2002/30616* (2013.01); *A61F 2002/30774* (2013.01); *A61F 2002/30785* (2013.01); *A61F 2002/4642* (2013.01); *A61F 2220/0025* (2013.01); *A61F 2220/0033* (2013.01)

(56) References Cited

U.S. PATENT DOCUMENTS

| | | | |
|---|---|---|---|
| 3,534,731 A * | 10/1970 | Muller | 606/105 |
| 3,686,896 A * | 8/1972 | Rutter | 464/52 |
| 4,106,128 A | 8/1978 | Greenwald et al. | |
| 4,211,228 A | 7/1980 | Cloutier | |
| 4,594,018 A * | 6/1986 | Larsson et al. | 403/43 |
| 4,634,613 A * | 1/1987 | Potter | 428/20 |
| 5,004,367 A * | 4/1991 | Wood, Jr. | 403/46 |
| 5,018,900 A * | 5/1991 | Darrin | 403/267 |
| 5,133,760 A * | 7/1992 | Petersen et al. | 623/20.36 |
| 5,269,784 A * | 12/1993 | Mast | 606/288 |
| 5,290,288 A * | 3/1994 | Vignaud et al. | 606/292 |
| 5,397,360 A | 3/1995 | Cohen et al. | |
| 5,413,605 A * | 5/1995 | Ashby et al. | 623/20.34 |
| 5,429,447 A * | 7/1995 | Wood | 403/46 |
| 5,459,973 A * | 10/1995 | Baumann | 52/848 |
| 5,556,433 A | 9/1996 | Gabriel et al. | |
| 5,613,970 A | 3/1997 | Houston et al. | |
| 5,722,785 A * | 3/1998 | Diener | 403/202 |
| 5,782,920 A * | 7/1998 | Colleran | 623/20.34 |
| 5,782,921 A * | 7/1998 | Colleran et al. | 623/20.15 |
| 5,824,097 A | 10/1998 | Gabriel et al. | |
| 5,879,389 A * | 3/1999 | Koshino | 623/20.11 |
| 5,879,391 A * | 3/1999 | Slamin | 623/20.15 |
| 5,944,756 A | 8/1999 | Fischetti et al. | |
| 5,956,917 A * | 9/1999 | Reynolds | 52/655.1 |
| 5,989,261 A * | 11/1999 | Walker et al. | 606/102 |
| 6,063,122 A * | 5/2000 | O'Neil et al. | 623/18.11 |
| 6,071,311 A * | 6/2000 | O'Neil et al. | 623/20.15 |
| 6,080,024 A * | 6/2000 | Miller et al. | 439/812 |
| 6,102,951 A * | 8/2000 | Sutter et al. | 623/18.11 |
| 6,102,952 A * | 8/2000 | Koshino | 623/20.21 |
| 6,146,424 A | 11/2000 | Gray, Jr. et al. | |
| 6,149,687 A | 11/2000 | Gray, Jr. et al. | |
| 6,162,255 A | 12/2000 | Oyola | |
| 6,165,223 A * | 12/2000 | Metzger et al. | 623/20.27 |
| 6,171,342 B1 * | 1/2001 | O'Neil et al. | 623/20.15 |
| 6,214,052 B1 * | 4/2001 | Burkinshaw | 623/20.34 |
| 6,228,091 B1 | 5/2001 | Lombardo et al. | |
| 6,261,291 B1 * | 7/2001 | Talaber et al. | 606/281 |
| 6,306,172 B1 * | 10/2001 | O'Neil et al. | 623/20.15 |
| 6,595,993 B2 * | 7/2003 | Donno et al. | 606/71 |
| 6,613,092 B1 * | 9/2003 | Kana et al. | 623/20.15 |
| 6,620,168 B1 | 9/2003 | Lombardo et al. | |
| 6,764,413 B2 * | 7/2004 | Ho | 473/288 |
| 6,782,920 B2 | 8/2004 | Steinke | |
| 6,824,566 B2 | 11/2004 | Kana et al. | |
| 6,869,447 B2 * | 3/2005 | Lee et al. | 623/20.15 |
| 6,953,479 B2 | 10/2005 | Carson et al. | |
| 6,988,846 B2 * | 1/2006 | Vogt | 403/299 |
| 7,025,788 B2 * | 4/2006 | Metzger et al. | 623/20.15 |
| 7,083,652 B2 * | 8/2006 | McCue et al. | 623/20.34 |
| 7,094,239 B1 * | 8/2006 | Michelson | 606/70 |
| 7,153,326 B1 * | 12/2006 | Metzger | 623/20.15 |
| 7,182,786 B2 * | 2/2007 | Justin et al. | 623/20.15 |
| 7,303,563 B2 * | 12/2007 | Poyner et al. | 606/279 |
| 7,445,639 B2 * | 11/2008 | Metzger et al. | 623/20.15 |
| 7,451,930 B1 * | 11/2008 | Neff | 235/454 |
| 7,497,874 B1 * | 3/2009 | Metzger et al. | 623/20.15 |
| 7,544,211 B2 * | 6/2009 | Rochetin | 623/20.34 |
| 7,608,112 B1 * | 10/2009 | Kuczynski et al. | 623/22.11 |
| 7,691,150 B2 * | 4/2010 | Cronin et al. | 623/20.32 |
| 7,695,519 B2 * | 4/2010 | Collazo | 623/20.15 |
| 7,766,969 B2 * | 8/2010 | Justin et al. | 623/20.15 |
| 7,780,711 B2 * | 8/2010 | Orbay et al. | 606/287 |
| 7,799,086 B2 * | 9/2010 | Justin et al. | 623/20.32 |
| 7,806,936 B2 * | 10/2010 | Wright | 623/20.15 |
| 7,842,093 B2 * | 11/2010 | Peters et al. | 623/20.15 |
| 7,854,737 B2 * | 12/2010 | Daniels et al. | 606/102 |
| 7,857,858 B2 * | 12/2010 | Justin et al. | 623/20.34 |
| 7,901,433 B2 * | 3/2011 | Forton et al. | 606/250 |
| 7,959,639 B1 * | 6/2011 | McGovern et al. | 606/102 |
| 7,998,217 B1 * | 8/2011 | Brown | 623/20.15 |
| 7,998,218 B1 * | 8/2011 | Brown | 623/20.35 |
| 8,075,628 B2 * | 12/2011 | Justin et al. | 623/20.34 |
| 8,123,788 B2 * | 2/2012 | Michelson | 606/295 |
| 8,157,869 B2 * | 4/2012 | Metzger et al. | 623/20.36 |
| 8,241,367 B2 * | 8/2012 | Justin et al. | 623/20.34 |
| 8,287,600 B2 * | 10/2012 | Angibaud | 623/20.32 |
| 8,328,873 B2 * | 12/2012 | Metzger et al. | 623/20.28 |
| 8,366,782 B2 * | 2/2013 | Wright | 623/20.15 |
| 8,460,390 B2 * | 6/2013 | Biss et al. | 623/19.14 |
| 8,523,950 B2 * | 9/2013 | Dees et al. | 623/20.28 |
| 8,529,578 B2 * | 9/2013 | Daniels et al. | 606/102 |
| 8,540,775 B2 * | 9/2013 | Reich et al. | 623/20.15 |
| 8,562,616 B2 * | 10/2013 | May et al. | 606/88 |
| 8,608,751 B2 * | 12/2013 | Cronin et al. | 606/99 |
| 8,636,807 B2 * | 1/2014 | Komistek | 623/20.33 |
| 8,721,729 B1 * | 5/2014 | Lu | 623/20.15 |
| 8,845,745 B2 * | 9/2014 | Dees et al. | 623/20.32 |
| 2001/0047174 A1 * | 11/2001 | Donno et al. | 606/73 |
| 2001/0053935 A1 | 12/2001 | Hartdegen | |
| 2002/0120340 A1 * | 8/2002 | Metzger et al. | 623/20.15 |
| 2003/0055508 A1 * | 3/2003 | Metzger et al. | 623/20.15 |
| 2003/0074078 A1 * | 4/2003 | Doubler et al. | 623/22.42 |
| 2003/0083660 A1 * | 5/2003 | Orbay | 606/69 |
| 2003/0204263 A1 * | 10/2003 | Justin et al. | 623/20.15 |
| 2003/0204269 A1 * | 10/2003 | Gerbec et al. | 623/23.47 |
| 2004/0068324 A1 * | 4/2004 | Grundei | 623/32 |
| 2004/0073315 A1 * | 4/2004 | Justin et al. | 623/20.15 |
| 2004/0087951 A1 * | 5/2004 | Khalili | 606/69 |
| 2004/0220572 A1 * | 11/2004 | Michelson | 606/71 |
| 2005/0015153 A1 * | 1/2005 | Goble et al. | 623/23.46 |
| 2005/0071014 A1 * | 3/2005 | Barnett et al. | 623/19.14 |
| 2005/0107883 A1 * | 5/2005 | Goodfried et al. | 623/20.15 |
| 2005/0187637 A1 * | 8/2005 | Karrer et al. | 623/22.24 |
| 2005/0283153 A1 * | 12/2005 | Poyner et al. | 606/61 |
| 2005/0283253 A1 * | 12/2005 | Coon et al. | 623/20.35 |
| 2006/0030945 A1 * | 2/2006 | Wright | 623/20.15 |
| 2006/0142867 A1 * | 6/2006 | Metzger et al. | 623/20.15 |
| 2006/0161157 A1 * | 7/2006 | Mosca et al. | 606/69 |
| 2006/0189998 A1 | 8/2006 | Rasmussen | |
| 2006/0233601 A1 * | 10/2006 | Crain et al. | 403/300 |
| 2006/0265079 A1 | 11/2006 | D'Alessio, II | |
| 2007/0010890 A1 * | 1/2007 | Collazo | 623/20.15 |
| 2007/0129808 A1 * | 6/2007 | Justin et al. | 623/20.15 |
| 2007/0150065 A1 | 6/2007 | Angibaud | |
| 2007/0162145 A1 * | 7/2007 | Justin et al. | 623/20.32 |
| 2007/0179628 A1 * | 8/2007 | Rochetin | 623/20.34 |
| 2008/0021566 A1 * | 1/2008 | Peters et al. | 623/20.16 |
| 2008/0097614 A1 * | 4/2008 | Wright | 623/20.15 |
| 2008/0114462 A1 * | 5/2008 | Guidera et al. | 623/20.27 |
| 2008/0147196 A1 * | 6/2008 | Cronin et al. | 623/20.34 |
| 2008/0147203 A1 * | 6/2008 | Cronin et al. | 623/27 |
| 2008/0159825 A1 * | 7/2008 | Tegg | 411/262 |
| 2008/0167722 A1 * | 7/2008 | Metzger et al. | 623/20.36 |
| 2008/0177337 A1 | 7/2008 | McGovern et al. | |
| 2008/0306603 A1 * | 12/2008 | Reich et al. | 623/20.15 |
| 2009/0005876 A1 * | 1/2009 | Dietz et al. | 623/20.36 |
| 2009/0088862 A1 * | 4/2009 | Thomas et al. | 623/20.36 |
| 2009/0125114 A1 * | 5/2009 | May et al. | 623/19.14 |
| 2009/0149963 A1 * | 6/2009 | Sekel | 623/20.15 |
| 2009/0149964 A1 * | 6/2009 | May et al. | 623/20.15 |
| 2009/0187251 A1 * | 7/2009 | Justin et al. | 623/20.34 |
| 2009/0299482 A1 * | 12/2009 | Metzger et al. | 623/20.29 |
| 2010/0152858 A1 * | 6/2010 | Lu et al. | 623/20.32 |
| 2010/0174378 A1 * | 7/2010 | Metzger et al. | 623/20.28 |
| 2010/0222891 A1 * | 9/2010 | Goodfried et al. | 623/20.36 |
| 2010/0262253 A1 * | 10/2010 | Cipolletti et al. | 623/20.28 |
| 2011/0009973 A1 * | 1/2011 | Meyers et al. | 623/20.32 |
| 2011/0054626 A1 * | 3/2011 | Thomas et al. | 623/20.36 |
| 2011/0066249 A1 * | 3/2011 | Justin et al. | 623/20.32 |
| 2011/0071642 A1 * | 3/2011 | Moussa | 623/20.14 |

(56) References Cited

U.S. PATENT DOCUMENTS

| | | | |
|---|---|---|---|
| 2011/0137425 A1* | 6/2011 | Allard et al. | 623/20.21 |
| 2011/0295377 A1* | 12/2011 | Dees et al. | 623/20.32 |
| 2011/0313534 A1* | 12/2011 | Ries et al. | 623/20.27 |
| 2012/0059484 A1* | 3/2012 | Justin et al. | 623/20.34 |
| 2012/0296438 A1* | 11/2012 | Metzger et al. | 623/20.29 |
| 2013/0150858 A1* | 6/2013 | Primiano et al. | 606/80 |
| 2013/0289634 A1* | 10/2013 | Meek et al. | 606/86 R |
| 2013/0304222 A1* | 11/2013 | Liu et al. | 623/20.33 |
| 2013/0345766 A1* | 12/2013 | McCleary et al. | 606/86 R |
| 2014/0067077 A1* | 3/2014 | Collard | 623/20.32 |
| 2014/0114318 A1* | 4/2014 | May et al. | 606/85 |
| 2014/0276883 A1* | 9/2014 | Matyas et al. | 606/99 |
| 2014/0277546 A1* | 9/2014 | Major et al. | 623/20.33 |
| 2014/0277550 A1* | 9/2014 | Lindsay et al. | 623/20.36 |
| 2014/0277551 A1* | 9/2014 | Lindsay et al. | 623/20.36 |
| 2015/0012106 A1* | 1/2015 | Dees et al. | 623/20.32 |

OTHER PUBLICATIONS

Brochure entitled Monogram® Total Knee Instruments Modular Rotating Hinge Knee System—Keel Baseplate Using Monogram® IM Revision Instruments, Stryker Howmedica Osteonics, pp. 1, 15-17 (2000).

Brochure entitled Ascent™ Total Knee System Revision Surgical Technique, Taking total knee replacement to new heights, Biomet Orthopedics, Inc., pp. 1, 16, 17 (2001).

* cited by examiner

TRIAL COUPLER SYSTEMS AND METHODS

CROSS REFERENCE TO RELATED APPLICATIONS

This application is the United States national phase of International Application No. PCT/US2006/042706 filed on Oct. 31, 2006 and published in English on Oct. 11, 2007 as International Publication No. WO 2007/114841 A1, which application claims the benefit of U.S. Provisional Application Ser. No. 60/789,177 filed on Apr. 4, 2006, the entire contents of both of which are hereby incorporated by reference.

BACKGROUND OF THE INVENTION

In total knee joint replacement surgery, a surgeon typically affixes two prosthetic components to a patient's bone structure: a first to the patient's femur and a second to the patient's tibia. These components are typically known as the femoral component and the tibial component, respectively.

The femoral component is placed on a patient's distal femur after appropriate resection. One common type of femoral component, the condylar component, features a J-shaped cross section, with an anterior face and two condylar portions. The femoral component is usually attached to a femoral stem which is received in the patient's intramedullary femoral canal.

A common type of tibial component uses a tray or plate that generally conforms to the patient's resected proximal tibia. The tibial component is usually attached to a tibial stem which is received in the patient's intramedullary tibial canal.

The tibial plateau and the condyles of the femur bearing on the tibial plateau act similar to a hinge within the knee to allow bending and movement of the knee. The tibial component and the femoral component ultimately cooperate with each other to replicate as closely as possible the action and relationship of the tibial plateau and the condyles of the femur bearing on it. A plastic or polymeric (often ultra high molecular weight polyethylene or UHMW) insert or bearing may fit between the plate of the tibial component and the femoral component. This insert or bearing provides a surface against which the femoral component condylar portions articulate (i.e., move in gross motion corresponding generally to the motion of the femur relative to the tibia).

Accurately positioning and fitting the prosthetic components is important for a number of reasons. Each patient has a different bone structure and geometry. Dynamically, motion of the tibia relative to the femur about every axis varies from one patient to the next. Even though the surgeon uses various imaging techniques and palpation to study a particular patient's anatomy, she nevertheless gains considerable additional information required to fit the prosthetic components after the knee has been surgically exposed and surgery is underway.

Trial prostheses are conventional for, among other things, trying the fit of prosthesis or implant components to respective portions of the joint. After shaping the femur and the tibia, the surgeon may temporarily fit trial components instead of the actual prosthetic components to the femur and/or tibia, respectively. This enables the surgeon to test the fit of the components to the femur and tibia and to test their performance both statically and dynamically throughout a desired range of motion. Use of trial prosthetics instead of actual implants also allows the surgeon to perform this testing and achieve a more perfect fit and a more accurate performance of the actual implant component without introducing a number of "new" actual prosthetic components into the surgical field.

Using actual, final prosthetic components for this fitting procedure is undesirable. Using trial prosthetic components instead of the actual implants allows the surgeon to position, move, and fit components while trying various sizes and, if desired, while modifying bone structure, without imparting wear and tear on actual implant components—upon which destruction could have adverse long-term effects. Additionally, the use of trial components keeps the implants from requiring re-sterilization if they are used and a new size is needed. Therefore, trial components, such as trial tibial components, trial femoral components, and trial stems, are initially used. The actual tibial and femoral implants are then assembled based on these trial components and implanted into the knee.

When a stem that is not offset is used and an offset is needed, the outside component can overhang or underhang, and thus adjustability is needed based on individual anatomy.

In addition to being offset from the mechanical axis, the tibial and femoral canals may be angled with respect to the mechanical axis of the leg. Across a population of humans, a valgus bowing of the tibia exists relative to the mechanical axis. Consequently, if a stem oriented parallel to the mechanical axis of the leg is inserted into a bowed tibial canal, the stem can impinge on the lateral cortex of the tibial canal proximal to the knee and the medial cortex distal to the knee. Similarly, the femoral canal can bow posteriorly relative to the mechanical axis, which results in impingement by the stem of the anterior cortex of the femoral canal in the diaphysis of the femur and the posterior cortex slightly superior to the knee. Such impingement can prevent adequate penetration of the canal by the stem and result in improper positioning of the tibial and femoral components in the knee.

Improper positioning of the component with respect to the bone can have adverse effects, including stress shielding and bone loss due to non-uniform transfer of load from the bone to the stem. It can also limit range of motion. Insertion of a stem into an angled tibial canal may result in misalignment of the tibial component with the tibial plateau so that a part of the tibial component hangs over the tibial plateau. Such overhang can lead to the tibial component rubbing the soft tissue surrounding the knee, causing irritation and pain. Moreover, a consequence of overhang by one side of the tibial component is underhang by the other side of the tibial component, so that the underhang portion of the component is resting on the softer cancellous bone instead of the harder cortical bone along the peripheral rim of the tibial plateau. The component may consequently sink into the softer bone, causing the entire component to tilt toward the side of the underhang. This can jeopardize the stability of the implant.

To accommodate such offset and/or bowed canals, stem extensions have been designed to connect tibial and/or femoral components to corresponding stems using rotational adjustment systems. These rotational adjustment systems result in a trial and error process where the surgeon sets the stem extension to a predetermined, discrete position and inserts the components into the patient's canal to determine if the assembly fits correctly. If the trial prosthesis with the stem extension does not align with the geometry of the patient's intramedullary canal, the surgeon removes the components from the patient's canal, resets the rotation position, and repositions the stem extension at a different preset position. This process is repeated until one of the preset positions best aligns with the geometry of the patient's canal. Such a trial and error process increases the time spent in the operating room and increases the possibility of damage to the bone due to repeated entry and exit of the intramedullary canal, as well as increased opportunity for infection. Moreover, other systems that do not use preset positioning also have problems because they fail to provide a way to lock the desired orientation. Accordingly, it is likely that the orientation determined using such systems will be disrupted when the trial prosthesis is removed from the patient. If this occurs, the final implant that is constructed based on the trial prosthesis will not be oriented correctly. Thus, such systems do not always allow for a perfect match with the anatomy of the patient's intramedullary canal, and improvements are necessary.

SUMMARY

Embodiments of the present invention provide a trial coupler system that allows a trial stem to be offset and/or angled in relation to the respective trial components at an orientation that matches the geometry of the patient. As used herein, the term "trial components" may be used to refer to a tibial trial component, a femoral trial component, or any other appropriate trial component that cooperates with the trial couplers described. Although various embodiments of the present invention are applicable to a variety of joint prosthetic components such as shoulders, elbows, ankles, and hips, and other joints, the embodiments are described for exemplary purposes with respect to a tibial and femoral component of a knee joint prosthesis. Embodiments of the present invention provide a coupler system that allows for the precise positioning of a trial stem and its corresponding trial component so that the assembled prosthesis aligns with the geometry of the patient's joint, i.e., the stem in the patient's intramedullary canal is appropriately positioned with respect to the trial component placed on the resected bone.

Embodiments of the present invention also allow a surgeon to better match the specific anatomy of a patient without restricting the orientation of the components to a predetermined position or being limited by components that do not lock when the proper position is determined and the trial system is to be removed. In certain embodiments, there is provided a coupling device (which may either be provided as a separate offset component that attaches to a trial stem if an offset is needed or may be provided as the upper portion of the stem) that is associated with a trial component interface that receives a trial component. The interface is adapted to rotate around the coupling device in order to allow the surgeon to position the relationship between the stem and the trial components precisely. Once the desired position is achieved, the surgeon can lock this orientation while the system is still on the patient so that the trial coupler can be removed from the patient without disturbing the orientation. Because the coupler system allows for an unlimited range of motion, the surgeon can initially determine the correct orientation to match the geometry of the patient's intramedullary canal with respect to one or more trial components without the need for repetition, and then lock the components in place.

According to one aspect of certain embodiments of the present invention, there is provided a trial coupler system, comprising (a) a coupling device adapted to receive a trial stem and cooperate with a trial component interface;

(b) a trial component interface adapted to cooperate with a trial component and the coupling device;

(c) a fastener adapted to secure the coupling device to the trial component interface, allowing the trial component interface to rotate relative to the coupling device; and (d) a rotational lock member adapted to lock rotational freedom between the coupling device and the trial component interface.

In one embodiment, the coupling device is an offset coupler.

In another embodiment, there is provided a spring to secure a trial stem in place.

In a further embodiment, the coupling device has an upper portion with a first longitudinal axis and a lower portion with a second longitudinal axis.

Other embodiments provide the fastener with a threaded shaft wherein the coupling device has a threaded portion that can receive the threaded shaft of the fastener.

A further embodiment provides the coupling device with an upper portion that is adapted to receive a connection member of the trial component interface.

Other embodiments provide a washer. Further embodiments provide a retention pin adapted to be inserted into the trial component interface to secure components and prevent disassembly.

Another embodiment provides a trial stem adapted to be secured with the coupling device.

Yet further embodiments comprise a trial component adapted to be secured with the trial component interface. In some embodiments, the trial component is a femoral component. In other embodiments, the trial component is a tibial component.

Other embodiments provide a trial component interface that comprises a trial connection system. In some embodiments, the trial connection system comprises a J-hook and protrusion connection, a ball-and-detent lock, a threaded connection, a dovetail slot and connection, a snap lock connection, a push lock connection, or a magnetic connection.

Further embodiments relate to a trial coupler system in which the trial stem is bowed, bent, angled, offset, or any combination thereof.

A further embodiment includes a trial coupler system wherein the coupling device, trial component interface, fastener, and rotational lock member are provided in a preassembled state, and in order to lock the system together, the rotational lock member is adapted to be tightened.

Another aspect of the invention relates to a trial coupler system, comprising:

(a) an offset coupling device having an inner cavity defined by an upper portion, a threaded portion, and a lower portion, the upper portion adapted to cooperate with a trial component interface, the threaded portion adapted to receive a fastener, and the lower portion adapted to receive a trial stem;

(b) a trial component interface having a trial connection system adapted to cooperate with a trial component and a connection member adapted to be received by the upper portion the offset coupling device, the trial component interface having a threaded bore ending in a lower ledge;

(c) a fastener having a head and a threaded shaft, the fastener adapted to be inserted into the threaded bore of the trial component interface such that the head abuts the lower ledge of the interface and the shaft extends through the threaded bore and into the inner cavity threaded portion of the offset coupling device; the fastener adapted to secure the offset coupling device to the trial component interface, allowing the trial component interface to rotate relative to the coupling device; and (d) a rotational lock member adapted to be inserted into the threaded bore of the trial component interface and secure against the fastener in order to lock rotational freedom between the offset coupling device and the trial component interface.

One embodiment of such a system further comprises a washer intended to be disposed between the fastener and the rotational lock member.

Another aspect of the present invention relates to a method for aligning a trial component with a trial stem in a patient, comprising:

(a) providing a trial coupler system, comprising
  (i) a coupling device adapted to receive a trial stem and cooperate with a trial component interface;
  (ii) a trial component interface adapted to cooperate with a trial component and the coupling device;
  (iii) a fastener adapted to secure the coupling device to the trial component interface, allowing the trial component interface to rotate relative to the coupling device; and
  (iv) a rotational lock member adapted to lock rotational freedom between the coupling device and the trial component interface;

(b) securing the trial coupler system to a trial stem at one end and a trial component at another end;

(c) determining an appropriate position between the trial stem and the trial component by rotating trial component interface with respect to coupling device;

(d) once the appropriate position is achieved, locking trial coupler system in place using rotational lock member.

One embodiment of such a method uses an offset coupling device.

Another embodiment includes the trial stem secured to the coupling device via a spring that is associated with the lower portion of the coupling device.

A further embodiment provides the trial connection system as comprising a J-hook and protrusion connection, a ball-and-detent lock, a threaded connection, a dovetail slot and connection, a snap lock connection, a push lock connection, or a magnetic connection.

Another aspect of the invention relates to a method for aligning a trial component with a trial stem in a patient, comprising:

(a) providing a trial stem having a coupling device at its proximal end having an inner cavity defined by an upper portion, a threaded portion, and a lower portion, (b) providing a trial component interface having a trial connection system and a connection member, the trial component having a threaded bore ending in a lower ledge, and nested in the trial component interface is (i) a fastener having a head and a threaded shaft and (ii) a rotational lock member, wherein the fastener is inserted into the threaded bore of the trial component interface such that the head of the fastener abuts the lower ledge;

(c) securing a trial component to the trial component interface via the trial connection system;

(d) inserting the connection member of the trial component interface into the upper portion of the trial stem coupling device;

(e) securing the threaded shaft of the fastener with the threaded portion of the coupling device, such that it secures the coupling device to the trial component interface and allows the trial component interface to rotate relative to the coupling device;

(f) securing the rotational lock member against the fastener in order to lock rotational freedom between the trial stem coupling device and the trial component interface.

"Embodiment" as used herein can be considered to mean an "aspect" or "object of the invention" and vice versa.

DETAILED DESCRIPTION OF THE INVENTION

Embodiments of the present invention provide a trial coupler system that facilitates positioning of a trial stem in a patient's intramedullary canal by matching the geometry of the trial stem and trial components with the geometry of the patient's intramedullary canal. Once this position is obtained, the orientation can be locked while the system is still on the patient's bone. This positioning can be achieved upon the surgeon's first entry into the bone instead of requiring trial and error to find the correct fit using predetermined placements.

Use of the systems described provides maneuverability in the placement of the trial stem with respect to the trial component, but also allows for the desired orientation to be locked while the system is on the bone. Then, the entire system (including the trial stem, trial coupler, and trial component) can be removed from the patient without the possibility of displacement. Once the trial system is removed from the patient, an implant assembly can be constructed or determined using the trials as a reference.

Generally, trial coupler devices according to various embodiments of the invention feature a coupling device (that can either cooperate with the end of a trial stem or be the end of the trial stem itself) and a trial component interface that cooperates with a trial component. The coupling device and interface are adapted to rotate around one another and then be rotationally locked once a desired relationship between the trial stem and the trial component is achieved.

Figure 1:
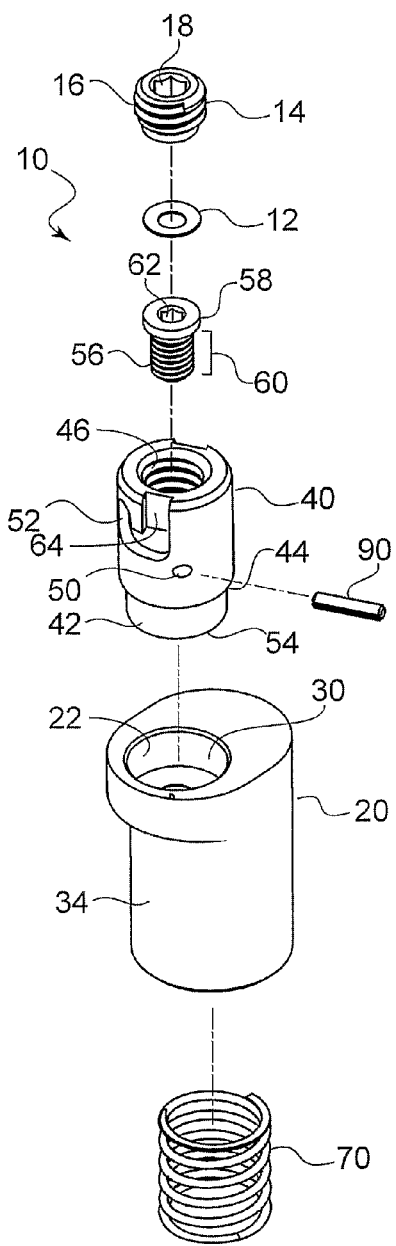
FIG. 1 is an exploded perspective view of one embodiment of the present invention for use with an offset trial stem.
Figure 2:
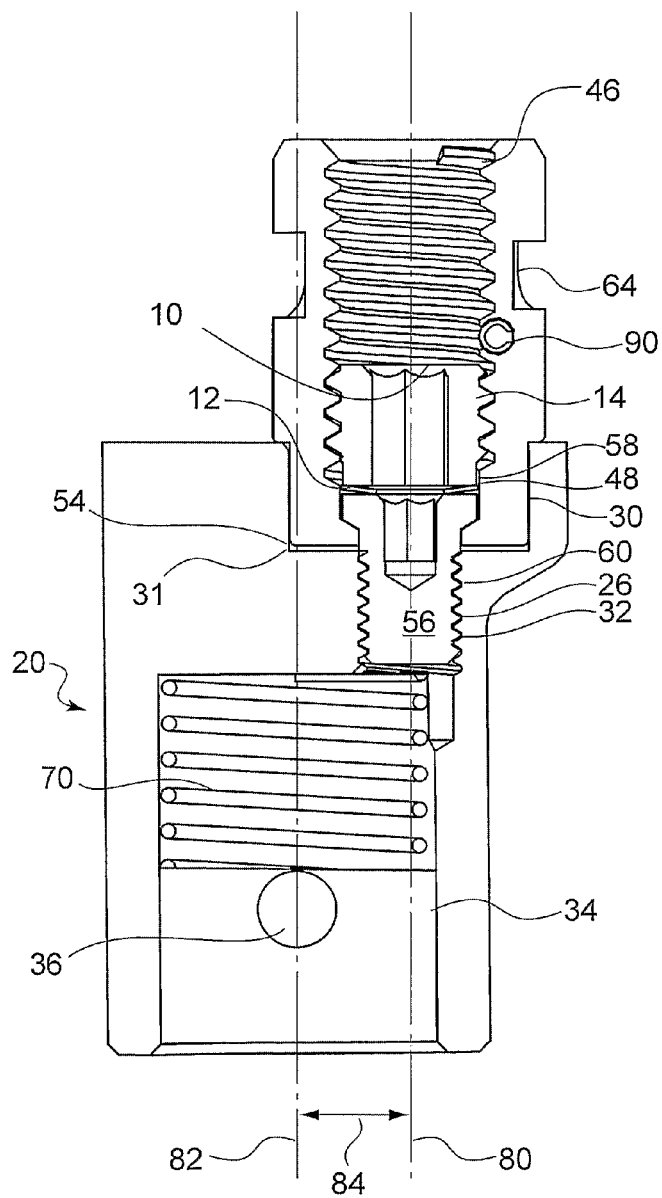
FIG. 2 is a cross-sectional view of the assembled system of FIG. 1.
Figures 3, 4:
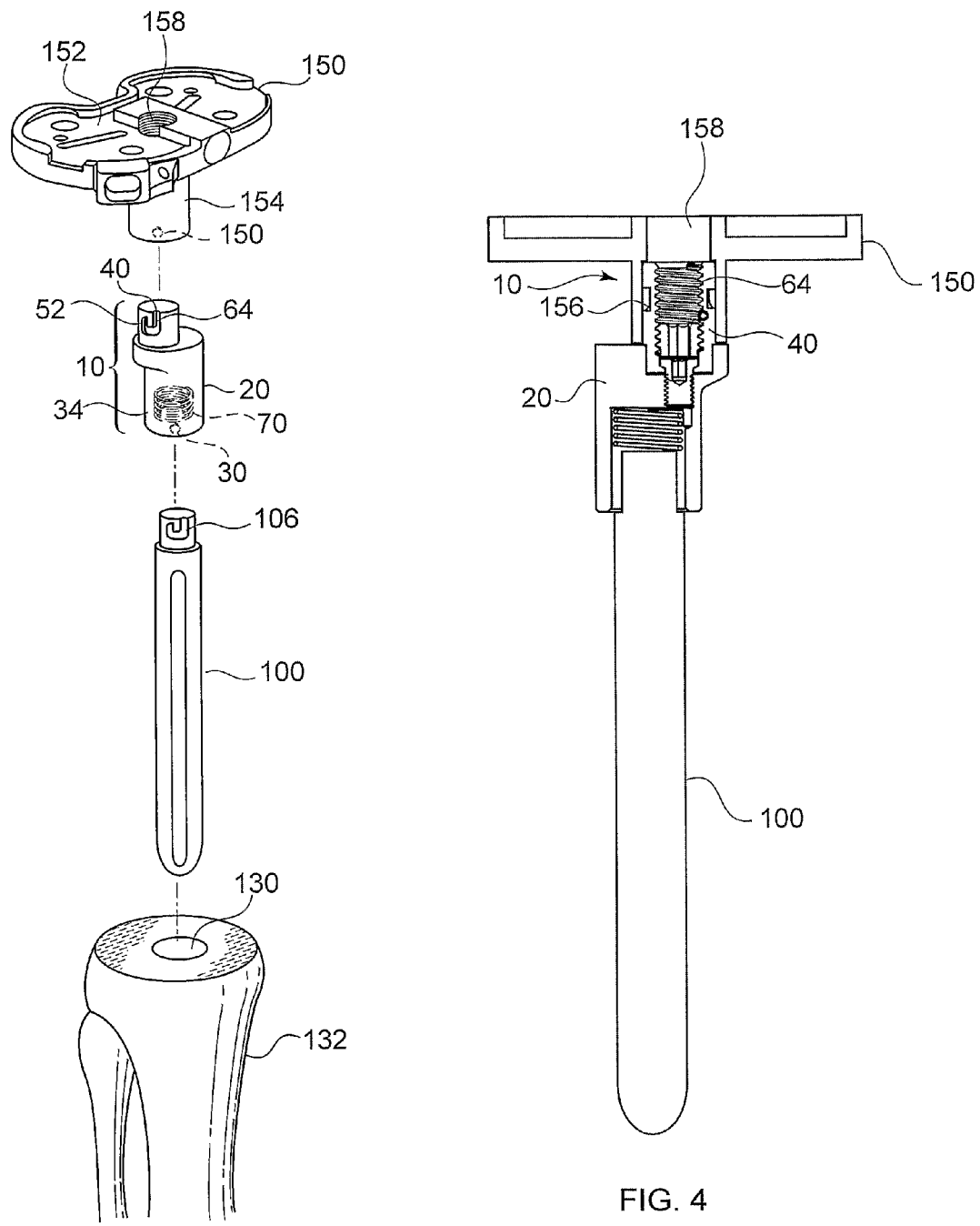
FIG. 3 is an exploded perspective view of one embodiment of the present invention in use with a tibial trial stem.
FIG. 4 is a cross-sectional view of the assembly of FIG. 3 in an assembled position.
Figure 6:
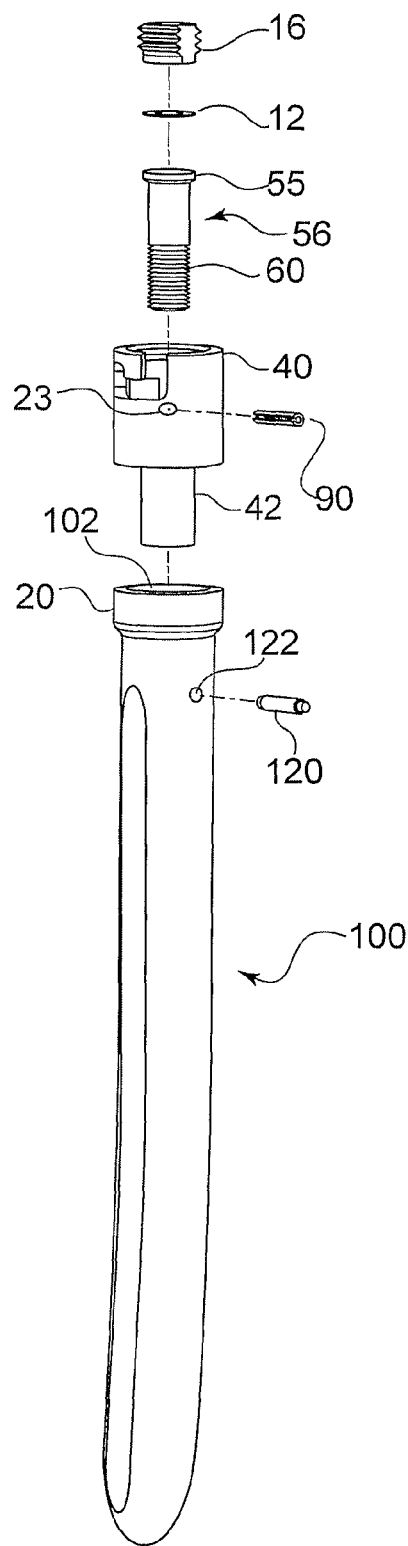
FIG. 6 is an exploded perspective view of an alternate embodiment of the present invention for use with a trial stem.
Figure 7:
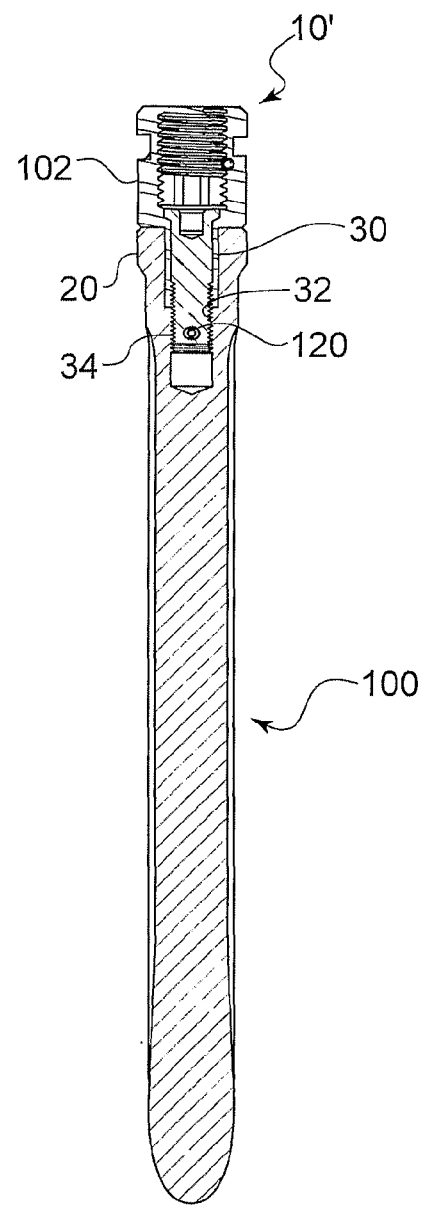
FIG. 7 is a cross-sectional view of the assembled system of FIG. 6.

If the trial stem should be offset with respect to the mechanical axis of the leg, one embodiment of the invention provides a trial coupler system 10 that includes an offset coupling device 20 as a connection end, as shown in FIGS. 1-2 and 4. If the trial stem does not need to be offset, another embodiment of the invention provides a neutral trial coupler system 10' that uses the proximal end of the trial stem as the coupling device, as shown in FIGS. 6-7. Although not described in detail, it is also understood that trial coupler systems described herein may impart an angle (e.g., 1 to 2 degrees or more or less) to the components it is used to secure, specifically to the trail stem. This may be accomplished by providing an angled coupling device (instead of or in addition to the offset coupling devices described).

Referring now to FIG. 1, there is shown an offset coupling device 20 and a trial component interface 40. These components are intended to be seated with respect to one another such that they can rotate relative to one another. Specifically, offset coupling device 20 has an inner cavity 22 that has an upper portion 30, a threaded portion 32, and a lower portion 34. The cross-section shown in FIG. 2 illustrates these elements more clearly. Of relevance for this discussion is the upper portion 30 of cavity 22. Upper portion 30 is offset from the longitudinal axis of device 20, providing a desired amount of offset. It has a shape that corresponds to the connection member 42 at a lower portion of trial component interface 40. In use, connection member 42 is inserted into upper portion 30 such that a ledge 44 of interface 40 sits on an upper surface 24 of device 20, and a base 54 of connection member 42 rests on an upper portion ledge 31, shown in FIG. 2.

Upper portion 30 and connection member 42 are shown as cylindrical or round, but it should be understood that they may be any corresponding shape that allows the two components 20, 40 to rotate freely with respect to one another. It should also be understood that offset coupling device 20 could have a connection member extending from its upper surface 24 that cooperates with a cavity in trial component interface 40. Other securement mechanisms are also within the scope of this invention, as long as they allow the two components to be rotationally associated.

Components 20 and 40 may be secured together by a fastener 56. Fastener 56 has a head 58 and a threaded shaft 60. As shown in FIG. 2, fastener 56 is inserted into a bore 46 of interface 40 (which is typically threaded), and fastener head 58 rests on a lower ledge portion 48 of interface 40 at its distal surface. In certain embodiments, the fastener head 58 has a smaller diameter than the inner diameter of threaded bore 46 so that it can slide easily down into the bore and seat head 58 against ledge portion 48. Threaded shaft 60 extends out of base 54 of connection member 42, and it engages the threaded portion 32 of inner cavity 22 of offset coupling device 20.

The threaded shaft 60 preferably corresponds to threads 26 on the threaded portion 32 of inner cavity 22. These corresponding threads may be provided in any number of shapes (e.g., trapezoidal teeth, triangular teeth, square teeth), pitches, and rotations (e.g., tightly wound around fastener or "loosely" wound such that there is a great distance between each thread). In short, fastener 56 serves to secure interface 40 and device 20 together so that they can be rotated, but prevents them from being separated from one another once threaded shaft 60 engages threaded portion 32 of coupling device 20. In other words, once fastener 56 is placed through interface 40 and partially tightened into the threads 26 of device 20, the head 58 of fastener sits on a lower ledge 48 of interface, and allows interface 40 to rotate independently of the coupling device 20 (e.g., while device 20 remains stationary). Fastener 56 has a bore 62 formed in its head 58 that can receive a securing instrument in order to secure it in place. Bore 62 may be any appropriate size or shape, such as a star-shape, a hex shape, a Phillips head shape or any other potential bore shape that allows it to receive a corresponding securing instrument.

FIG. 1 also shows an optional washer 12. If used, washer 12 may be assembled into the bore 46 of interface 40 and placed between fastener 56 and rotational lock member 14, described below. Washer 12 can help provide relief from torsional displacement of coupling device 20 and interface 40. Although washer 12 is shown as circular in shape, it should be understood that it may any appropriate shape or thickness that allows it be used as intended.

When components 20 and 40 are secured together by fastener 56, they can be maneuvered as needed until the desired relationship between a trial stem and a trial component (between which the trial coupler system 10 is located) is achieved. In certain embodiments, the system 10 is provided in its pre-assembled state. In other words, interface 40 is nested within coupling device 20 and fastener 56 holds them together. Rotational lock member 14 is them inserted above them. Once manufactured, the entire system can be held together with an optional retention pin 90 that can be inserted during manufacture to help prevent disassembly during transit. Retention pin 90 can be pressed through a retention pin receiving opening 50 in interface 40 to keep the assembled components in position. It is intended to rest just above rotational lock member 14 to prevent it from working loose during the trialing process. Although the optional retention pin 90 is shown as cylindrical or round, it should be understood that it could be any number of shapes, lengths, or widths, as long as it corresponds to and can be secured in retention pin receiving opening 50.

The system 10 may be provided in its preassembled state, with retention pin 90 holding components together and with rotational lock member 14 somewhat loosened so that the surgeon can rotate interface 40 with respect to coupling device 20. Then, once the proper position has been located, the surgeon will need to lock the coupling device 20 and interface 40 in place. This can be done through the use of a rotational lock member 14. Rotational lock member 14 has a threaded surface 16 that is adapted to correspond to the threaded bore 46 of interface 40. Threaded surface may be provided in any number of shapes (e.g., trapezoidal teeth, triangular teeth, square teeth), pitches, and rotations (e.g., tightly wound around connection member or "loosely" wound such that there is a great distance between each thread), as long as the threaded surface 16 of rotational lock member 14 corresponds to and can be secured within the threaded bore 46 of interface 40. Rotational lock member 14 also has a bore 18 formed at its upper end that can receive a securing instrument in order to secure it in place. Bore 18 may be any appropriate size or shape, such as a star-shape, a hex shape, a Phillips head shape or any other potential bore shape that allows it to receive a corresponding securing instrument. In use, once rotational lock member 14 is secured in threaded bore 46, it can be tightened by a securing instrument so that it locks the rotational freedom between interface 40 and offset coupling device 20. In other words, when rotational lock member 14 is tightened, it squeezes against the head 58 of fastener 56 and restricts the movement of interface 40 relative to coupling device 20. When the rotational lock member 14 is loosened, interface 40 is then allowed to freely rotate about device 20, even when device 20 remains stationary.

Reference will now be made to how the coupling device 20 and the trial component interface 40 are coupled to a trial stem and a trial component, respectively. As shown in FIGS. 1 and 2, coupling device 20 has an inner cavity 22 with a lower portion 34. Lower portion 34 can receive a spring 70, which provides an optional way of connecting trial coupler system 10 to a trial stem. Spring 70 can provide resistance to help prevent the trial stem from wobbling in its connection with device 20. In one embodiment, lower portion 34 of inner cavity 22 may have a protrusion 36 that is adapted to press against the bottom of spring 70. Protrusion 36 may also engage a J-hook 106 on a trial stem 100 as shown in FIGS. 3 and 4. In use, trial stem 100 is inserted into lower portion 34 of inner cavity 22. The protrusion 36 engages an upper part of the J-hook 106, and as the stem is advanced further into device 20, the J-hook receives the protrusion 36 along the contour of the "J." When the stem is turned, the connection is locked. As the J-hook 106 engages protrusion 36, the spring 70 is compressed so that it holds the tension against the trial stem.

The above description is just one way that the offset coupling device 20 can be secured to a trial stem. It should be understood that in addition, any other type of connection is within the scope of this invention, for example, the connection may be achieved via a ball-and-detent lock, a threaded connection, a dovetail slot and connection, a snap or push lock connection, a magnetic connection, or any other appropriate connection that can hold the two components together securely. In any of these connections, the use of a spring may be beneficial, but it is not necessary.

The trial component interface 40 may be likewise secured to a femoral or tibial component (or any other trial component to be used) by a trial connection system 52. In the embodiment shown in FIGS. 1-3, the trial connection system 52 is a J-hook 64 system much like the one described above. There may be a J-hook 64 located on the external surface of the interface 40, and in some embodiments, both sides may feature a J-hook, as shown in the cross-section of FIG. 2. This hook may be secured with one or more protrusions 156 that are located inside an extension 154 extending from the trial component 150. However, it should also be understood that any of the alternate mating connections described above may also be used.

As discussed, FIG. 2 shows the components described above in an assembled configuration. As shown in this particular embodiment, the upper portion 30 of the offset coupling device 20 has a first longitudinal axis 80 and the lower portion 34 defines a second longitudinal axis 82. The distance 84 between the two axes represents an amount of offset between a patient's intramedullary canal and the patient's tibial plateau and/or the patient's femoral condyles that can be achieved using an offset coupling device 20. In some embodiments, that offset is 2, 4, 6, 8, or 10 mm, although it may be more or less, depending upon the particular design. If multiple offset options are needed, it is possible to provide multiple offset coupling devices 20 having varying offsets. For example, a first device 20 could have a 2 mm offset, a second device could have a 4 mm offset and so forth. Offsets may also be provided in intermediate ranges, such as 2.5, 4.5, and any other appropriate values.

FIG. 3 illustrates an exploded view of an embodiment of the trial coupler system 10 to be used with a tibial trial stem 100 and a tibial component 150. Tibial component 150 has a plate 152 and an extension 154 extending from its bottom surface. Extension 154 may have a protrusion 156 on its inner surface that cooperates with J-hook 64 of interface 40, as described above, although other connection mechanisms are also possible and considered within the scope of this invention.

When the trial coupler system 10 is in a loosened state (i.e., the rotational lock member 14 has not been engaged), the surgeon can rotate the interface 40 around the offset coupling device 20 to correspond to the geometry of the intramedullary canal 130 of the patient's tibia 132. Once the desired position is achieved, the rotational lock member 14 is secured as described above. Specifically, the surgeon may insert a securing instrument through an opening 158 in tibial plate 152 so that components can be secured into inner cavity 22 and bore 46. FIG. 4 shows an example of the completed tibial system locked in place.

Figure 5:
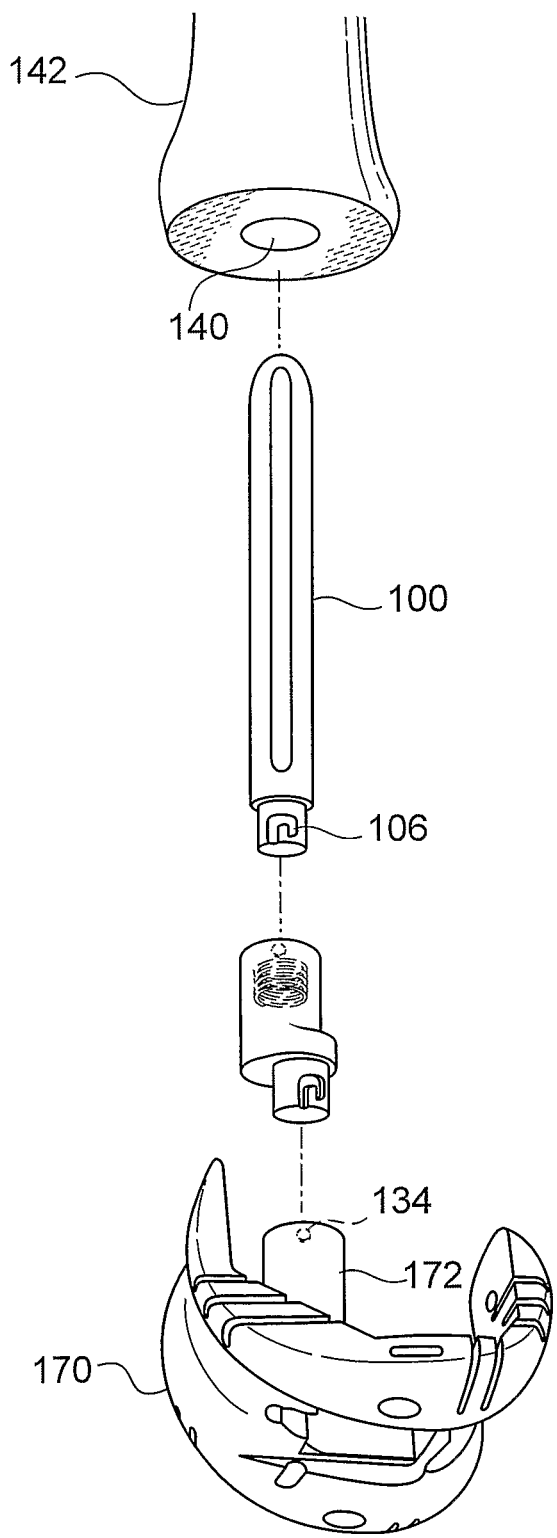
FIG. 5 is an exploded perspective view of one embodiment of the present invention in use with a femoral trial stem.

FIG. 5 illustrates an embodiment of the trial coupler system 10 to be used with a femoral stem 100 and a femoral component 170. (Although tibial and femoral trial stems obviously have different features, they are referred to collectively in this document as trial stem 100 for the purposes of discussion.) Similar to tibial component 150, femoral component 170 has an extension 172 (sometimes referred to as a stem extension) extending from its inner surface. Again, a protrusion 174 may be located inside the extension 172 for connection with J-hook 64 (as described above, alternate connection mechanisms may be used). In use, the trial coupler system 10 is again loosened and tightened via action of the rotational lock member 14 so that the system can be configured to correspond to the geometry of the intramedullary canal 140 of the patient's femur 142 and then be locked in place.

In use, the method for aligning a trial component with a trial stem in a patient can include the surgeon selecting a trial coupler system 10 having a coupling device. The device 10 is attached to a trial stem and a trial component. In some embodiments, the trial stem may be secured to the coupling device via a spring that is associated with the lower portion of the coupling device. In some other embodiments the trial component interface may be secured to a trial component (via the trial connection system) by a J-hook and protrusion connection, a ball-and-detent lock, a threaded connection, a dovetail slot and connection, a snap lock connection, a push lock connection, or a magnetic connection. The surgeon determines the appropriate position between the trial stem and component by rotation interface 40 with respect to coupling device 20, and once the appropriate position is achieved, the surgeon locks system 10 in place using rotational lock member 14. This locks rotational freedom between the offset coupling device and the trial component interface.

FIGS. 6 and 7 illustrate an alternate embodiment of a trial coupler system 10' that can be used where an offset is not needed. In short, system 10' omits the offset coupling device 20 and uses the proximal end 102 of the trial stem 100 as the coupling device 20 to receive trial component interface 40. The trial stem of FIG. 6 is shown as bowed, which is often necessary for use with certain patients, but it should be understood that any type of stem can be used within the scope of this invention. Examples of potential trial stem designs are those that are bowed, bent, angled, offset, or any combination thereof. The proximal end 102 of trial stem should have features similar to that described for the offset coupling device 20, except that upper portion 30 is not offset. Specifically, as shown in FIG. 7, proximal end 102 has an upper portion 30, a threaded portion 32, and a lower portion 34, except that upper portion 30 and lower portion 34 share the same longitudinal axis. The remaining discussion above can be applied to the cooperation between trial stem 100 and interface 40. However, one difference is that fastener 56 is shown as being more elongated than the fastener of FIG. 1. In addition, connection member 42 of trial component interface 40 may also be more elongated. It should be understood that other dimensions of other components may also change.

Another additional feature shown in FIGS. 6 and 7 is an optional retention pin 120 that can be inserted through an opening 122 in the trial stem 100. As with optional retention pin 90, optional retention pin 120 may help to hold the assembly together by preventing fastener 56 from loosening. Optional retention pin 120 is shown as cylindrical or round in shape, but it should be understood that any number of shapes, lengths or widths can be used with the scope of the invention.

In use, the method for aligning a trial component with a trial stem in a patient for this embodiment can include the surgeon selecting a trial stem having a coupling device at its proximal end having an inner cavity defined by an upper portion, a threaded portion, and a lower portion, and then selecting a trial component interface having a trial connection system and a connection member, the trial component having a threaded bore ending in a lower ledge. The interface is provided with a fastener and a rotational lock member. With the surgeon using the trial stem end as the coupling device, the remaining method steps described above are similar here.

Changes and modifications, additions and deletions may be made to the structures and methods recited above and shown in the drawings without departing from the scope or spirit of the invention and the following claims.

What is claimed is:

1. A trial coupler system, comprising:
   a tibial tray;
   a coupling device defining an inner cavity;
   a trial component interface configured to removably couple to the tibial tray, the trial component interface having a connection member configured to be received within the inner cavity, the trial component interface defining a bore having a single central axis, the bore extending through the trial component interface;
   a fastener configured to be received within the bore and the inner cavity to couple the trial component interface and the coupling device, the fastener adapted to allow the trial component interface to rotate relative to the coupling device upon fully seating the fastener;
   a lock member having external threads for engaging a threaded portion of the bore to restrict relative rotational movement of the trial component interface and the coupling device; and
   a trial stem adapted to be removably coupled to the coupling device.

2. The trial coupler system of claim 1, wherein the inner cavity includes a portion configured to receive the trial stem.

3. The trial coupler system of claim 1, wherein with the tibial tray rotationally locked with respect to the trial component interface, the lock member is adapted to be tightened via an opening in the tibial tray to lock rotational freedom between the coupling device and the trial component interface.

4. A trial coupler system, comprising:
   a femoral condylar component;
   a coupling device defining an inner cavity;
   a trial component interface configured to removably couple to the femoral condylar component, the trial component interface having a connection member configured to be received within the inner cavity, the trial component interface defining a bore having a single central axis, the bore extending through the trial component interface;
   a fastener configured to be received within the bore and the inner cavity to couple the trial component interface and the coupling device, the fastener adapted to allow the trial component interface to rotate relative to the coupling device upon fully seating the fastener;
   a lock member having external threads for engaging a threaded portion of the bore to restrict relative rotational movement of the trial component interface and the coupling device; and
   a trial stem adapted to be removably coupled to the coupling device.

5. The trial coupler system of claim 4, wherein the inner cavity includes a portion configured to receive the trial stem.

6. The trial coupler system of claim 4, wherein with the femoral condylar component rotationally locked with respect to the trial component interface, the lock member is adapted to be tightened via an opening in the femoral condylar component to lock rotational freedom between the coupling device and the trial component interface.

7. A trial coupler system, comprising
   (a) a trial stem;
   (b) a trial component;
   (c) a coupling device adapted to removably couple to the trial stem, wherein the coupling device has a threaded portion;
   (d) a trial component interface adapted to cooperate with the coupling device and removably couple to the trial component, wherein one of the trial component interface and the coupling device includes a connection member configured to be received by the other of the trial component interface and the coupling device to rotationally couple the trial component interface and the coupling device;
   (e) a fastener having a threaded shaft adapted to be received by the threaded portion, the fastener adapted to secure the coupling device to the trial component interface and to allow the trial component interface to rotate relative to the coupling device upon fully seating the fastener; and
   (f) a rotational lock member adapted to be inserted into the trial component interface to lock rotational freedom between the coupling device and the trial component interface.

8. The trial coupler system of claim 7, wherein the coupling device is an offset coupler.

9. The trial coupler system of claim 7, wherein the coupling device has an upper portion that is adapted to receive the connection member of the trial component interface.

10. The trial coupler system of claim 7, wherein with the trial component rotationally locked with respect to the trial component interface, the rotational lock member is adapted to be tightened via an opening in the trial component to lock rotational freedom between the coupling device and the trial component interface.

11. A trial coupler system, comprising
    (a) a trial stem;
    (b) a tibial tray;
    (c) a coupling device adapted to removably couple to the trial stem;
    (d) a trial component interface adapted to cooperate with the coupling device and removably couple to the tibial tray, wherein one of the trial component interface and the coupling device includes a connection member configured to be received by the other of the trial component interface and the coupling device to rotationally couple the trial component interface and the coupling device;
    (e) a fastener adapted to secure the coupling device to the trial component interface and to allow the trial component interface to rotate relative to the coupling device upon fully seating the fastener; and
    (f) a rotational lock member adapted to be inserted into the trial component interface to lock rotational freedom between the coupling device and the trial component interface.

12. The trial coupler system of claim 11, wherein the coupling device is an offset coupler.

13. The trial coupler system of claim 11, further comprising a spring to secure the trial stem in place.

14. The trial coupler system of claim 11, wherein the coupling device has an upper portion with a first longitudinal axis and a lower portion with a second longitudinal axis offset from the first longitudinal axis.

15. The trial coupler system of claim 11, wherein the fastener has a threaded shaft and wherein the coupling device has a threaded portion that can receive the threaded shaft of the fastener.

16. The trial coupler system of claim 11, wherein the coupling device has an upper portion that is adapted to receive the connection member of the trial component interface.

17. The trial coupler system of claim 11, further comprising a washer disposed between the fastener and the rotational lock member.

18. The trial coupler system of claim 11, further comprising a retention pin inserted in the trial component interface to secure components.

19. The trial coupler system of claim 11, wherein the trial component interface comprises a trial connection system.

20. The trial coupler system of claim 19, wherein the trial connection system is selected from the group consisting of a J-hook and protrusion connection, a ball-and-detent lock, a threaded connection, a dovetail slot and connection, a snap lock connection, a push lock connection, and a magnetic connection.

21. The trial coupler system of claim 11, wherein the trial stem is selected from the group consisting of bowed, bent, angled, and offset trial stems.

22. The trial coupler system of claim 11, wherein the coupling device, trial component interface, fastener, and rotational lock member are provided in a pre-assembled state, and in order to lock the system together, the rotational lock member is adapted to be tightened.

23. The trial coupler system of claim 11, wherein with the tibial tray rotationally locked with respect to the trial component interface, the rotational lock member is adapted to be tightened via an opening in the tibial tray to lock rotational freedom between the coupling device and the trial component interface.

24. A trial coupler system, comprising
(a) a trial stem;
(b) a femoral condylar component;
(c) a coupling device adapted to removably couple to the trial stem;
(d) a trial component interface adapted to cooperate with the coupling device and removably couple to the femoral condylar component, wherein one of the trial component interface and the coupling device includes a connection member configured to be received by the other of the trial component interface and the coupling device to rotationally couple the trial component interface and the coupling device;
(e) a fastener adapted to secure the coupling device to the trial component interface and to allow the trial component interface to rotate relative to the coupling device upon fully seating the fastener; and
(f) a rotational lock member adapted to be inserted into the trial component interface to lock rotational freedom between the coupling device and the trial component interface.

25. The trial coupler system of claim 24, wherein the coupling device is an offset coupler.

26. The trial coupler system of claim 24, further comprising a spring to secure the trial stem in place.

27. The trial coupler system of claim 24, wherein the coupling device has an upper portion with a first longitudinal axis and a lower portion with a second longitudinal axis offset from the first longitudinal axis.

28. The trial coupler system of claim 24, wherein the fastener has a threaded shaft and wherein the coupling device has a threaded portion that can receive the threaded shaft of the fastener.

29. The trial coupler system of claim 24, wherein the coupling device has an upper portion that is adapted to receive the connection member of the trial component interface.

30. The trial coupler system of claim 24, further comprising a washer disposed between the fastener and the rotational lock member.

31. The trial coupler system of claim 24, further comprising a retention pin inserted in the trial component interface to secure components.

32. The trial coupler system of claim 24, wherein the trial component interface comprises a trial connection system.

33. The trial coupler system of claim 32, wherein the trial connection system is selected from the group consisting of a J-hook and protrusion connection, a ball-and-detent lock, a threaded connection, a dovetail slot and connection, a snap lock connection, a push lock connection, and a magnetic connection.

34. The trial coupler system of claim 24, wherein the trial stem is selected from the group consisting of bowed, bent, angled, and offset trial stems.

35. The trial coupler system of claim 24, wherein the coupling device, trial component interface, fastener, and rotational lock member are provided in a pre-assembled state, and in order to lock the system together, the rotational lock member is adapted to be tightened.

36. The trial coupler system of claim 24, wherein with the femoral condylar component rotationally locked with respect to the trial component interface, the rotational lock member is adapted to be tightened via an opening in the femoral condylar component to lock rotational freedom between the coupling device and the trial component interface.

37. A trial coupler system, comprising:
(a) a trial stem;
(b) a trial component;
(c) an offset coupling device having an inner cavity defined by an upper portion, a lower portion, and a threaded portion between the upper and lower portions, the lower portion adapted to removably couple to the trial stem;
(d) a trial component interface adapted to cooperate with the upper portion and having a trial connection system adapted to removably couple to the trial component, the trial component interface having a connection member adapted to be received by the upper portion of the inner cavity, the trial component interface having a threaded bore ending in a lower ledge;
(e) a fastener having a head and a threaded shaft, the fastener adapted to be inserted into the threaded bore of the trial component interface such that the head abuts the lower ledge of the interface and the shaft extends through the threaded bore and into the inner cavity threaded portion of the offset coupling device, the fastener adapted to secure the offset coupling device to the trial component interface and to allow the trial component interface to rotate relative to the coupling device upon fully seating the fastener; and
(f) a rotational lock member adapted to be inserted into the threaded bore of the trial component interface and secure against the fastener in order to lock rotational freedom between the offset coupling device and the trial component interface.

38. The trial coupler system of claim 37, further comprising a washer intended to be disposed between the fastener and the rotational lock member.

39. The trial coupler system of claim 37, wherein with the trial component rotationally locked with respect to the trial component interface, the rotational lock member is adapted to be tightened via an opening in the trial component to lock rotational freedom between the coupling device and the trial component interface.

* * * * *